US011547954B2

(12) United States Patent
Bruder et al.

(10) Patent No.: US 11,547,954 B2
(45) Date of Patent: *Jan. 10, 2023

(54) COMPOUND EXTRACTION FROM PLANT BASED MATERIAL UTILIZING TEREPENE SATURANT

(71) Applicant: Chimera Technology LLC., Palatine, IL (US)

(72) Inventors: Geoffrey A. Bruder, Rocky River, OH (US); Shelby Griebel, Waterloo, IL (US); David Flood, Palatine, IL (US)

(73) Assignee: CHIMERA TECHNOLOGY LLC., Palatine, IL (US)

( * ) Notice: Subject to any disclaimer, the term of this patent is extended or adjusted under 35 U.S.C. 154(b) by 142 days.

This patent is subject to a terminal disclaimer.

(21) Appl. No.: 17/078,263

(22) Filed: Oct. 23, 2020

(65) Prior Publication Data

US 2021/0121795 A1 Apr. 29, 2021

Related U.S. Application Data

(60) Provisional application No. 62/925,823, filed on Oct. 25, 2019.

(51) Int. Cl.
*B01D 11/02* (2006.01)
*A61K 36/18* (2006.01)
(Continued)

(52) U.S. Cl.
CPC ........ *B01D 11/0288* (2013.01); *A61K 36/185* (2013.01); *B01D 11/0292* (2013.01); *C11B 3/001* (2013.01)

(58) Field of Classification Search
CPC ........... B01D 11/0288; B01D 11/0292; B01D 11/0211; B01D 11/0257; B01D 11/0265;
(Continued)

(56) References Cited

U.S. PATENT DOCUMENTS 4,946,695 A * 8/1990 Forster ............... B01D 11/0292
426/429
6,061,926 A 5/2000 Paré et al.
(Continued)

FOREIGN PATENT DOCUMENTS

WO WO2019211794 A1 * 11/2019 ............. B01D 11/02

OTHER PUBLICATIONS

Daniela De Vita et al., "Comparison of Different Methods for the Extraction of Cannabinoids from Cannabis," Natural Product Research, ISSN: 1478-6427, Apr. 29, 2019.

*Primary Examiner* — Joseph W Drodge
(74) *Attorney, Agent, or Firm* — Flener IP & Business Law; Zareefa B. Flener

(57) ABSTRACT

A method for extracting compounds from plant material utilizing terpenes as a solvent is described. The invention includes the excitation of the plant material and terpene solvent with microwave, ultrasound, heat input, and physical agitation or combinations thereof. The invention particularly covers the process as it relates to the extraction of THC and CBD and their derivatives from cannabis and hemp for the use in products for medical and recreational use. The combinations of terpene saturant, plant material strain and process variables can be tuned in order to dial in the final resultant product for several variables including but not limited to terpene content, THC or CBD potency, ratios of THC or CBD and their derivatives, or flavor profile.

9 Claims, 2 Drawing Sheets

(51) Int. Cl.
*C11B 3/00* (2006.01)
*A61K 36/185* (2006.01)

(58) Field of Classification Search
CPC ... B01D 1/00; B01D 3/10; B01D 9/00; B01D 9/0018; B01D 9/0059; B01D 11/0203; B01D 11/0261; B01D 11/028; B01D 15/08; B01D 15/12; B01D 15/125; B01D 36/00; B01D 36/02; B01D 39/06; B01D 39/2055; B01D 39/2058; A61L 2/005; A61L 2/0011; A61L 2/0017; A61L 2/0047; A61L 2/0064; A61L 2/02; A61L 2/022; A61L 2/10; A61L 2/12; A61L 2/202; A61L 2202/21; F26B 5/06; C11B 1/02; C11B 1/025; C11B 1/04; C11B 1/10; C11B 1/104; C11B 1/108; C11B 3/00; C11B 3/001; C11B 3/003; C11B 3/005; C11B 3/006; C11B 3/008; C11B 3/08; C11B 3/12; C11B 3/16; C12N 11/18; A61K 36/00; A61K 36/16; A61K 36/185; A61K 36/268; A61K 36/53; A61K 36/532; A61K 36/62; A61K 36/896; A61K 36/906; A61K 36/9066; C07C 37/004; C07C 39/23; C07C 45/78; C07C 45/79; C07C 45/81; C07C 45/82; C07C 45/85; C07C 49/248; C07C 49/255
USPC ........... 210/634, 638, 748.1, 760, 770, 774; 424/725, 728, 752, 756, 774; 554/8, 20, 554/21, 22, 175, 206; 435/132, 175, 267, 435/271

See application file for complete search history.

(56) References Cited

U.S. PATENT DOCUMENTS

| | | | |
|---|---|---|---|
| 9,447,198 B2 | 9/2016 | Zhang et al. | |
| 10,143,706 B2 | 12/2018 | Kotra et al. | |
| 10,272,360 B2 | 4/2019 | Lopa | |
| 10,413,845 B1* | 9/2019 | Tegen | B01D 11/0288 |
| 10,537,592 B2 | 1/2020 | Kotra et al. | |
| 10,745,644 B1* | 8/2020 | Ellis | C11B 3/00 |
| 10,828,341 B2 | 11/2020 | Rivas | |
| 10,941,131 B1 | 3/2021 | Grondin et al. | |
| 10,946,308 B2 | 3/2021 | Hari et al. | |
| 10,961,174 B2 | 3/2021 | Tegen et al. | |
| 10,973,864 B2 | 4/2021 | Venturini Del Greco | |
| 11,253,793 B1* | 2/2022 | Thiel | B01D 11/0288 |
| 2009/0216007 A1* | 8/2009 | Zhang | C08B 37/006 536/128 |
| 2013/0338234 A1 | 12/2013 | Splinter et al. | |
| 2017/0008870 A1* | 1/2017 | Dibble | C07D 311/80 |
| 2020/0009205 A1* | 1/2020 | Rivas | A61K 36/185 |
| 2020/0063061 A1 | 2/2020 | Vanaman | |
| 2020/0324501 A1* | 10/2020 | Harrington | B30B 9/047 |
| 2020/0383893 A1 | 12/2020 | Ham et al. | |
| 2020/0398180 A1* | 12/2020 | Hospodor | B01D 5/0036 |
| 2020/0398184 A1 | 12/2020 | Farokhi et al. | |
| 2021/0094929 A1* | 4/2021 | Tegen | A61K 36/185 |
| 2021/0100864 A1 | 4/2021 | Ham et al. | |

* cited by examiner

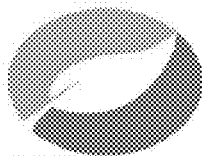

LK Pure Labs

LAB REPORT

Customer: Progressive Treatment Solutions, LLC
Address: 737 Locust St.
East St. Louis, IL 62201

Manifest ID: 3737440062657901
Sample: 2019-01-13 Test 34-1
Type: Hydrocarbon Wax
Batch/Lot ID: 2988 2821 6153 3863
Sample ID: 3025 9446 0706 7705

Received: 01/14/2019

Lab ID/Sample Report ID: 20190114PJ
Potency Test Results- WI-001 HPLC-UV

Analysis Date: 01/14/2019

| TEST | WEIGHT % | CONCENTRATION (mg/g) |
|---|---|---|
| CBD | 0.22% | 2.20 |
| CBG | <0.10% | <1.00 |
| CBD-A | <0.10% | <1.00 |
| CBN | <0.10% | <1.00 |
| Delta 9 THC (THC) | <0.10% | <1.00 |
| Delta 8 THC | <0.10% | <1.00 |
| CBC | <0.10% | <1.00 |
| THC-A | 0.02% | 0.20 |
| THC-V | <0.10% | <1.00 |
| TOTAL | 0.24% | 2.40 |

Terpene Test Results- GCMS       Analysis Date: 01/14/2019

| TEST | Microgram Per Gram (ug/g) | TEST | Microgram Per Gram (ug/g) |
|---|---|---|---|
| Alpha-Pinene | 10746.66 | Linalool | N.D. |
| Camphene | N.D. | Fenchyl Alcohol | N.D. |
| Sabinene | 1853.74 | Borneol | N.D. |
| Beta-Pinene | 5807.66 | Alpha Terpineol (isomer) | 246.50 |
| Beta-Myrcene | 44925.38 | Gamma Terpineol (isomer) | N.D. |
| Alpha-Phellandrene | N.D. | Beta-Caryophyllene | N.D. |
| Delta-3-Carene | N.D. | Elemene | N.D. |
| Alpha-Terpinene | N.D. | Alpha-Humulene | N.D. |
| P-Cymene | N.D. | Valencene | N.D. |
| Limonene | 99069.11 | Cis-Nerolidol | N.D. |
| Eucalyptol | N.D. | Trans Nerolidol | N.D. |
| Ocimene | N.D. | Caryophyllene Oxide | N.D. |
| Gamma-Terpinene | N.D. | Guaiol | N.D. |
| Sabinene Hydrate | N.D. | Alpha-Bisabolol | N.D. |
| Terpinolene | N.D. | | |
| Fenchone | N.D. | Total Terpenes | 162649.04 |

Figure 1

COMPOUND EXTRACTION FROM PLANT BASED MATERIAL UTILIZING TEREPENE SATURANT

CROSS-REFERENCE TO RELATED APPLICATIONS

This application claims priority to U.S. Provisional Application Ser. No. 62/925,823 filed on Oct. 25, 2019, the disclosure of which is incorporated herein by reference in its entirety.

FIELD OF THE INVENTION

This invention relates to extraction of terpenes and cannabinoids from cannabis plant using terpenes as a solvent with or without excitation to aid the extraction.

BACKGROUND OF THE INVENTION

Extraction of chemical compounds from plants typically utilizes harsh chemicals which are expensive and can leave residual chemicals within the product for consumers. To remove the desired components from plant-based materials, the plant is often subjected to heat and pressure while submerged in a solvent such as Butane or Hexane. The solvent is then separated from the useable chemical by a secondary process which uses heat to evaporate the solvent.

Rather than using harsh chemicals to extract the useful plant compounds, for plants natively containing terpenes, a terpene can be used as the collection media. The plant-based material and terpene solvent, or "saturant", can be excited or agitated using ultrasound, microwave, heat, pressure, or a combination of these in order to achieve the desired extraction without the use of harsh chemicals. The process of terpene extraction leads to a clean, high purity extraction and, in the case of cannabinoids, is able to perform with near 100% efficiency with the appropriate combination of saturant and excitation.

BRIEF SUMMARY OF THE INVENTION

The subject invention includes the use of terpenes such as, but not limited to, D-Limonene, Myrcene, Phellandrene, Caryophyllene, and Alpha-Pinene for the extraction of compounds from plant-based materials, in particular, THC and CBD and their derivatives from cannabis or hemp. The plant material, include the leaves, stems, and buds can be removed from the plant and immediately processed, stored in a freezer or other controlled environment, or dried to remove moisture. Prior to extraction, the plant material may be further chilled to fractionate the plant and break down cell walls, leading the plant to more readily release the desired compounds. Furthermore, the plant material may be soaked in the terpene prior to extraction.

The extraction process may utilize an excitation method including microwave, ultrasound, heat input through radiation or conductive elements, or combinations of these methods. The subject invention also covers the use of physical agitation during the extraction process, such as a rotating stir mechanism or forced flow in the saturant. Furthermore, the temperature of the process may be controlled through an external chiller or ice bath of the processing volume. This serves the purpose of allowing the excitation energy to help release the desired compounds while keeping the process temperatures low enough to not degrade the compounds or approach the combustion temperature of the plant material or saturant.

Vacuum may be used in order to remove oxygen from the process, helping to maintain the integrity of the chemical compounds and reducing the likelihood of combustion by increasing flash temperatures and eliminating the oxidizer for the combustion process. Also, especially in the case of microwave excitation, vacuum allows for a larger pressure differential from inside the plant material to the processing volume which can increase the ability of the process to reclaim desired compounds or reduce the required processing time.

The combinations of terpene saturant, plant material strain and process variables can be tuned in order to dial in the final resultant product for several variables including but not limited to terpene content, THC or CBD potency, ratios of THC or CBD and their derivatives, or flavor profile. Particular effects can be achieved through the combinations of these variables leading to products that effect different outcomes on the patient including pain reduction, increased energy and decreased appetite.

BRIEF DESCRIPTION OF THE DRAWINGS

FIG. 1 shows a lab report from the extraction of CBD at ~100% efficiency from a CBD rich strain. THC is below detectable limit.

DETAILED DESCRIPTION AND BEST MODE OF IMPLEMENTATION

Figure 2:
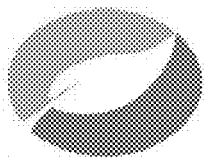
FIG. 2 shows a lab report from the extraction of THC-A at ~100% efficiency from a THC rich strain.

According to the first aspect of the invention removal of terpenes and cannabinoids from cannabis flower is conducted using 200-900 W/L of microwave energy utilizing a terpene or plurality of terpenes as the saturant.

According to the second aspect of the invention the plant material is stored in a sub-zero freezer and soaked in the saturant for up to 12 hours prior to extraction.

According to the third aspect of the invention the ratio of saturant to plant material is 0.02-1.0 g/L.

According to the fourth aspect of the invention a temperature of <30° C. is maintained through the use of an external chiller.

We claim:

1. A process for removal of terpenes and cannabinoids from plant material comprising the steps of:
   combining a saturant and the plant material; and
   exciting the saturant and the plant material using 200-900 W/L of microwave energy.

2. The process of claim 1 wherein the plant material is stored in a sub-zero freezer and soaked in the saturant for up to 12 hours prior to the exciting step.

3. The process of claim 1 wherein the saturant and the plant material are combined in a ratio of 0.02-1.0 g/L.

4. The process of claim 1 wherein a temperature of <30° C. is maintained throughout the process.

5. The process of claim 1 wherein the exciting step comprises using ultrasonic excitation along with the microwave energy simultaneously or sequentially.

6. The process of claim 1 wherein the process is conducted under vacuum.

7. The process of claim 1 wherein the cannabinoids are isolated without being decarboxylated.

8. The process of claim 1 wherein the exciting step heats the saturant and the plant material to a temperature above 30° C. in order to decarboxylate the cannabinoids.

9. The process of claim 1 where the saturant comprises a terpene or a plurality of terpenes.

\* \* \* \* \*

UNITED STATES PATENT AND TRADEMARK OFFICE
CERTIFICATE OF CORRECTION

| | |
|---|---|
| PATENT NO. | : 11,547,954 B2 |
| APPLICATION NO. | : 17/078263 |
| DATED | : January 10, 2023 |
| INVENTOR(S) | : Geoffrey A. Bruder, Shelby Griebel and David Flood |

It is certified that error appears in the above-identified patent and that said Letters Patent is hereby corrected as shown below:

On the Title Page

Item [54] and in the Specification Column 1 Line 1:
Delete "TEREPENE"
And insert --TERPENE--

Signed and Sealed this
Twenty-first Day of February, 2023

*Katherine Kelly Vidal*

Katherine Kelly Vidal
*Director of the United States Patent and Trademark Office*